(12) United States Patent
Booker

(10) Patent No.: US 7,251,982 B2
(45) Date of Patent: Aug. 7, 2007

(54) APPARATUS FOR ANALYSIS OF AEROSOLS

(75) Inventor: David R. Booker, Wantage (GB)

(73) Assignee: Sensors, Inc., Saline, MI (US)

( * ) Notice: Subject to any disclaimer, the term of this patent is extended or adjusted under 35 U.S.C. 154(b) by 104 days.

(21) Appl. No.: 10/989,035

(22) Filed: Nov. 15, 2004

(65) Prior Publication Data

US 2005/0172735 A1   Aug. 11, 2005

Related U.S. Application Data

(60) Provisional application No. 60/519,699, filed on Nov. 13, 2003.

(51) Int. Cl.
*G01N 15/00* (2006.01)
(52) U.S. Cl. .................... 73/24.03; 73/28.01; 73/28.04
(58) Field of Classification Search ............... 73/24.03, 73/28.01, 28.04, 865.5
See application file for complete search history.

(56) References Cited

U.S. PATENT DOCUMENTS

| | | | | |
|---|---|---|---|---|
| 2,675,697 A | * | 4/1954 | Quynn et al. ........... | 73/28.01 X |
| 3,395,516 A | * | 8/1968 | Schecter et al. ........ | 73/28.04 X |
| 3,653,253 A | * | 4/1972 | Olin ........................ | 73/24.03 |
| 3,879,986 A | * | 4/1975 | Sehmel ................... | 73/28.04 |
| 4,987,767 A | * | 1/1991 | Corrigan et al. ........ | 73/28.04 X |
| 5,834,628 A | * | 11/1998 | Hunter et al. ............ | 73/28.04 |
| 6,439,027 B1 | * | 8/2002 | Hiss, III .................. | 73/28.01 |
| 6,530,287 B1 | * | 3/2003 | Rodgers ................. | 73/28.04 X |
| 6,786,075 B2 | * | 9/2004 | Radke et al. ............ | 73/28.01 X |
| 6,796,164 B2 | * | 9/2004 | McLoughlin et al. .... | 73/28.01 |
| 2003/0123059 A1 | * | 7/2003 | Krempl et al. .......... | 356/338 |

* cited by examiner

*Primary Examiner*—Thomas P. Noland
(74) *Attorney, Agent, or Firm*—Van Dyke, Gardner, Linn & Burkhart, LLP

(57) ABSTRACT

There is provided apparatus for the measurement of particle mass concentration of an aerosol and which comprises at least one aerosol inlet and at least one electrostatic precipitator which directs an aerosol flow towards a mass sensor on which the particles are collected, the sensor being housed in a magazine including a plurality of other sensors, each of which may be substituted for the sensor, and a control. The control selectively connects one of the at least one aerosol inlet with one of the sensors.

18 Claims, 4 Drawing Sheets

APPARATUS FOR ANALYSIS OF AEROSOLS

CROSS REFERENCE TO RELATED APPLICATION

This application claims priority from U.S. provisional patent application Ser. No. 60/519,699, filed on Nov. 13, 2003, the disclosure of which is hereby incorporated herein by reference in its entirety.

BACKGROUND OF THE INVENTION

This invention relates to apparatus used for the analysis of the particles in an aerosol, and in particular measurement of particle mass concentration and size distribution of an aerosol.

Apparatus having piezoelectric crystal sensors have been used for a number of years to measure particle concentrations of aerosols. Such sensors are described in "The Performance of Piezo-Electric Crystal Sensors Used to Determine Aerosol Mass Concentration" by Daly S P and Lundgrun D A, American Industrial Hygiene Assoc. Journal, July, 1975, p518-532, Piezo-Electrostatic Aerosol Mass Concentration Monitor by Olin J G, Sem G J & Christenson D L, Amer. Ind. Hyg. Assoc. J. 32:209 (1970) and U.S. Pat. No. 3,653,253. Such apparatus include a piezoelectric crystal sensor which is exposed to a gas stream containing particles that deposit on the surface of the crystal. By measuring the frequency shift of the crystal and by knowing the mass sensitivity for the crystal, it is possible to determine the mass accumulated on the crystal surface. If the volume of the gas flow is known, the mass concentration can be determined.

A problem with the apparatus is that the crystal sensor can only function properly up to a maximum mass loading and, when used for environmental monitoring of particles, the sensor often becomes overloaded before the expiration of a standard test period; for example, a crystal sensor may overload in 1 or 2 days within a 14-day monitoring period for monitoring environmental particulates. Furthermore, the problems associated with the overloading of crystal sensors reduces the usefulness of such sensors for testing vehicle emissions.

The present invention provides improved apparatus which is useful for continuous monitoring of particulate concentrations, and which is also useful for the analysis of collected particles.

SUMMARY OF INVENTION

According to an aspect of the present invention, there is provided apparatus for the measurement of particle mass concentration of an aerosol and which comprises at least one aerosol inlet and at least one electrostatic precipitator which directs an aerosol flow towards a mass sensor on which the particles are collected, said sensor being housed in a magazine including a plurality of other sensors, each of which may be substituted for said sensor, and a control. The control selectively connects one of said at least one aerosol inlet with one of the sensors.

Each precipitator may be mounted in an aperture in a support, and the magazine may be movably mounted on the support so that sensors housed in the magazine may each be brought separately into alignment with a respective precipitator. The precipitator inlet may be provided with a heater which is controllable and may be used to vary the temperature of the aerosol flowing past the sensor.

The sensors in the illustrative embodiment are piezoelectric quartz crystals which may be in the form of discs.

The magazine may be in the form of a carousel with each sensor aligned with a respective precipitator by indexing the carousel relative to the support. The carousel may be rotatably mounted in a cylindrical recess in the support and is indexed by a motor, preferably a stepped motor, operated by said control means.

The at least one aerosol inlet may be a plurality of aerosol inlets. A valve assembly may be provided to selectively connect certain ones of the aerosol inlets with certain ones of the sensors. The valve assembly may be a rotary valve assembly that is rotated with an actuator, such as a stepper motor.

The sensor may be provided with a heater which is controllable to vary the temperature of the sensor which may be preset to any temperature as is desired. This allows the sensor to be used to weigh collected deposits after they have been subject to heat treatment.

The apparatus may have a plurality of precipitators, preferably two, each being aligned with a respective sensor. This configuration allows for two operations to be performed simultaneously, for example, one precipitator/sensor combination may be measuring particle concentration, and the other combination may be used for thermo-gravimetric analysis.

The Inlets of the two precipitators may differ in aerosol size classification performance, for example, in cross-section, or one may be provided with a particle remover, for different uses of the apparatus.

Yet another aspect of the invention provides apparatus for the measurement of particle mass concentration of an aerosol and which comprises at least one electrostatic precipitator which directs an aerosol flow onto a mass sensor on which the particles are collected, wherein the sensor is provided with a heater which is controllable to vary the temperature of the sensor which may be preset to any temperature as is desired.

Also, according to the invention, there is provided apparatus for the measurement of particle mass concentration of an aerosol, and which comprises at least one electrostatic precipitator which directs an aerosol flow onto a mass sensor on which the particles are collected, wherein each precipitator has an inlet provided with a heater which is controllable to vary the inlet temperature.

A further invention provides apparatus for the analysis of particles in an aerosol and which comprises a plurality of electrostatic precipitators which each direct an aerosol flow onto a respective mass sensor on which the particles are collected, wherein the respective inlets of said precipitators differ one from the other in aerosol size classification properties.

BRIEF DESCRIPTION OF THE DRAWINGS

The invention will be described by way of example and with reference to the accompanying drawings in which:

FIG. 1 is a schematic cross section through an aerosol electrostatic precipitator;

FIG. 2 is a schematic cross section through an apparatus for measuring the particle mass of an aerosol, according to the present invention;

FIG. 3 is a top plan view of a quartz crystal magazine as used in the apparatus of FIG. 2;

FIG. 4 is a schematic drawing of the control system of the apparatus shown in FIG. 2;

FIG. 5 is the same view as FIG. 2 of an alternative embodiment;

FIG. 6b is a bottom plan view of the rotating valve in FIG. 6a.

DESCRIPTION OF THE PREFERRED EMBODIMENT

Figure 1:
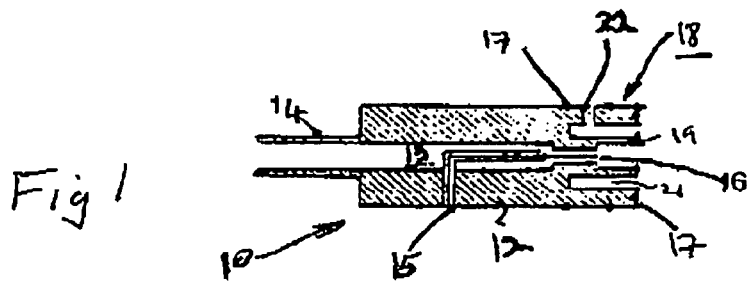
Figure 2:
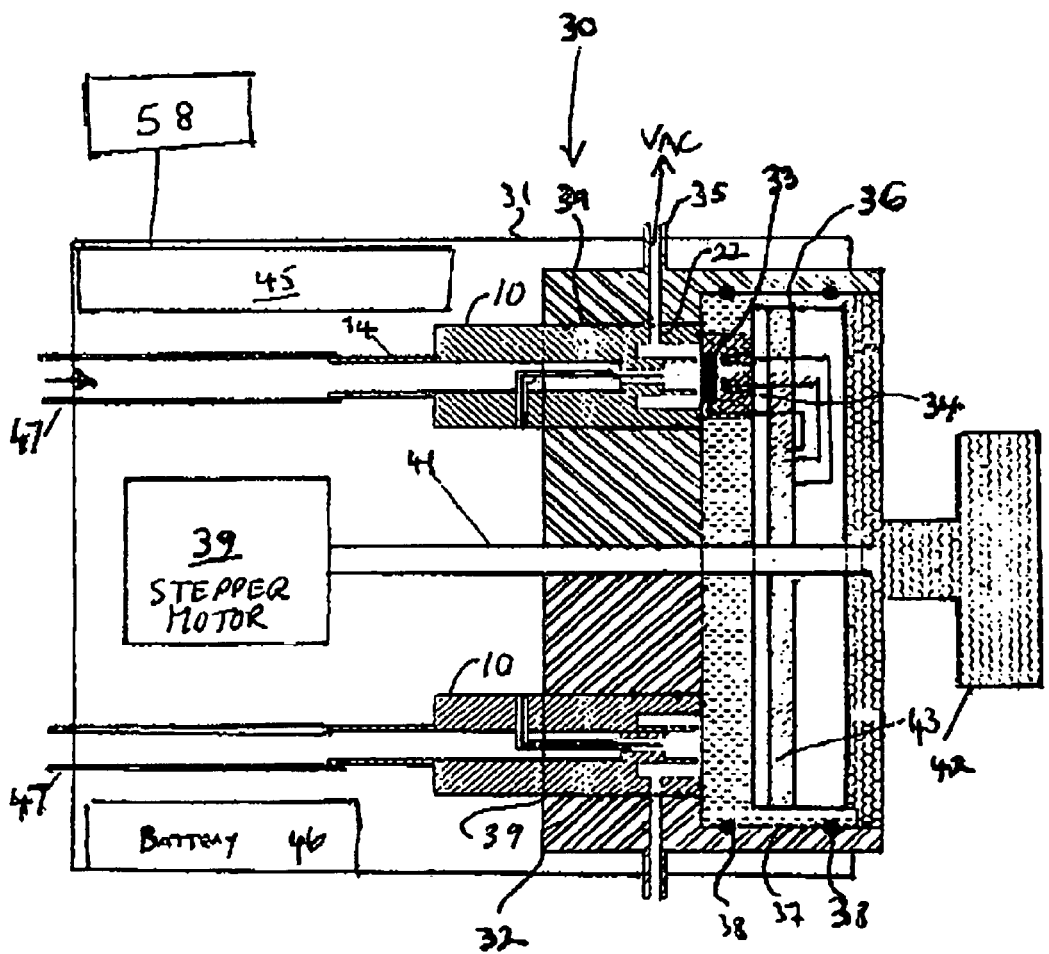
Figure 3:
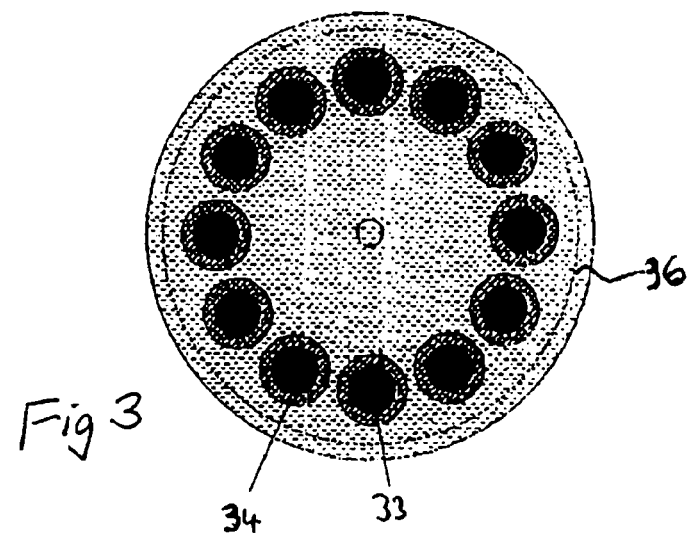
Figure 4:
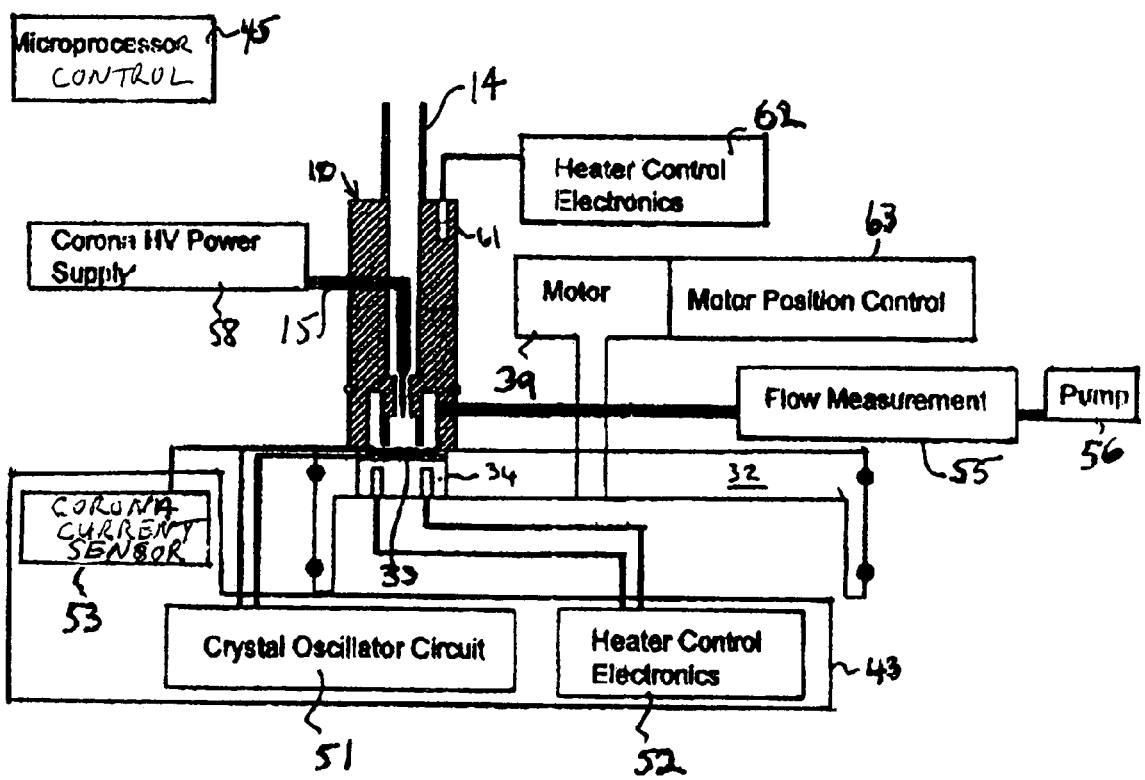

With reference to FIG. 1, there is shown an aerosol electrostatic precipitator 10 having a body 12 with a particle charging chamber 13 therein. The chamber 13 may have a temperature-controlled sample inlet tube 14 through which the aerosol is introduced into the chamber 13. The temperature controlled inlet 14 helps prevent cold aerosol from cooling the surface of a particle collector and prevents water vapor from being deposited. The inlet tube 14 may be made from an electrically conductive material in order to reduce losses of particles passing through. The tube dimensions are chosen to minimize particle losses and ensure that the aerosol may be heated to a required temperature.

A corona needle 16 is located within the chamber 13 and is connected to a high voltage power supply 58 (FIG. 4) via electrical conductors 15. The chamber body 12 is typically made from an electrically insulating material and its inner end portion 18 (that is inner with respect to the apparatus) is provided with a plurality of ring seals 17 to provide a gas tight seal with a support 32 (FIG. 2). The corona needle 16 is isolated from the body 12 and is usually easily removable for cleaning.

The inner end portion 18 of the body 12 has a hollow central spigot 19 which, in use, directs the charged aerosol flow onto a quartz crystal 33 (FIG. 2), and is surrounded by an outer annular space 21 which is conflicted to a radial outlet port 22 through which the aerosol exits the body 12. The outlet port 22 has seals 17 on each side thereof. Other configurations of an electrostatic precipitator may be used.

Now, with reference to FIG. 2, there is shown in schematic form apparatus 30 for measuring the particle mass of an aerosol. The apparatus includes a housing 31 which encloses at least one aerosol electrostatic precipitator 10 sealingly mounted on a support 32. The precipitator 10 is located in an aperture 39 in the support and is coaxially aligned with a quartz crystal 33 mounted in a metal holder 34. In use, as particles pass the needle 16, they pick up charges (positive or negative charging maybe used) from the intense ion field near the needle tip and are driven by the electric field toward the collection surface, in this case a quartz crystal surface. Electrostatic force is an effective means for particle collection especially for small submicrometer sized particles.

The o-rings 17 seal the precipitator 10 within the aperture 39 in the support 32 and against the crystal holder 34 and the gas flow exits the apparatus via outlet 22 and aligned exit passageway 35 in the support. In use, the exit passageway 35 is connected to a vacuum pump 56 (see FIG. 4).

With reference now also to FIG. 3, the holder 34 with its respective crystal 33 is one of a plurality of, preferably 12, such crystals and holders mounted in a magazine, preferably a carousel 36. The holders 34 are formed from an electrically conductive material and the crystals are removable from the respective holders for example, for analysis, for storage of the sample, cleaning, and the like. The quartz crystals 33 are preferably in the form of a disc, which, in the illustrative embodiment, are about 14 mm in diameter. The holders 34 are equiangularly spaced around the carousel 36 which is housed in a cylindrical recess 37 in the support 32 and is sealingly rotatable within the recess 37. Seals 38 on the outer surface of the carousel provide a gas tight seal with the radially inner surface of the recess and the carousel is rotated by a step motor 39 via a drive shaft 41. An external handle 42 is provided to enable the carousel to be both easily inserted into and removed from the support 32.

With reference now also to FIG. 4, a control system of apparatus 30 includes an electronic control 43 relating to the crystal 33. In the illustrative embodiment, control 43 is located within the carousel 36. The controls 43 include an oscillator circuit 51 to drive and measure the crystal frequencies, heater controls 52 for the crystal temperature, and sensors 53 for measurement of corona current on the crystal exposed to the aerosol. The controls 43 store calibration data for the crystals and are connected to a main control 45 and transmit data to the main control 45. The piezoelectric quartz crystal 33 is externally driven by the oscillator circuit 51 attached to two metal plates, preferably platinum or gold, located on either side of the crystal. This imposes a time-dependent electric field across the plates causing the crystal to oscillate. The resonant frequency is typically between 1 to 10 MHz, but may be outside of this range depending upon application.

The control system of apparatus 30 includes a main control 45. Control 45 may be located within the housing and may be provided within its own electrical power source 46, such as a long life battery. The control 45 may be accessed through an external computer (not shown), such as a PC. The inlet 14 for the precipitator is connected to external inlets 47.

The main control 45 for that apparatus is shown schematically in FIG. 4 and includes a main microprocessor control 45 which is connected to the carousel controls 43 as previously described, as well as to the other controls. For the sake of clarity, the lines linking the controls have been omitted. The aerosol flow through the precipitator 10 is monitored by a flow measure 55 connected to control 45 which also controls the vacuum pump 56. The field strength of the corona at the needle 16 is varied by control of the power supply 58 connected to conductors 15 and varied to provide a constant corona current. The temperature of the aerosol inlet 14 is controlled by means of a heater 61 and its controls 62. Rotation of the carousel 32 is controlled by a motor position control 63 which causes the step motor 39 to index the carousel to different positions to bring different crystals into alignment with the precipitator.

The plurality of crystal collectors allows the frequency of the crystals not exposed to the aerosol to be determined enabling the mass loss to be determined post aerosol exposure. Since this can be carried out at controlled crystal temperatures, this also enables a thermo-gravimetric analysis to be performed on particle deposits collected.

The apparatus may be provided with a plurality of precipitators 10, and preferably two, as shown in FIG. 2. This allows for different inlets to be selected for each precipitator. For example, different size inlets will give particle sizing information and, if one inlet is provided with a particle removal system, the apparatus will have a thermal gravimetric analysis capability allowing particle levels to be monitored at one location whilst thermo-gravimetric analysis is carried out at the second.

A second configuration 130 of an apparatus for analyzing particles in an aerosol is shown FIG. 5. In apparatus 130, there is provided apparatus for the measurement of particle mass concentration of an aerosol, but the said mass sensor is selected by a rotating multi-valve 67 mounted above the sensor magazine. This valve can be rotated using a stepper motor 65 or any other electromechanical means. Apparatus 130 may have a plurality of precipitators/inlet heaters, preferably eight, each being selectively aligned with a respective sensor. This configuration allows for multiple operations to be performed simultaneously, for example, one precipitator/sensor combination may be used for measuring the particle concentration, another may be used for thermogravimetric analysis and a third for a sample baseline determination (for example, humidity compensation). A cassette of filters 66 used for gravimetric or other additional measurements may be provided, such a cassette is located above the main body. These filters can be automatically selected to facilitate a simultaneous collection of the sampled aerosol.

Figure 5:
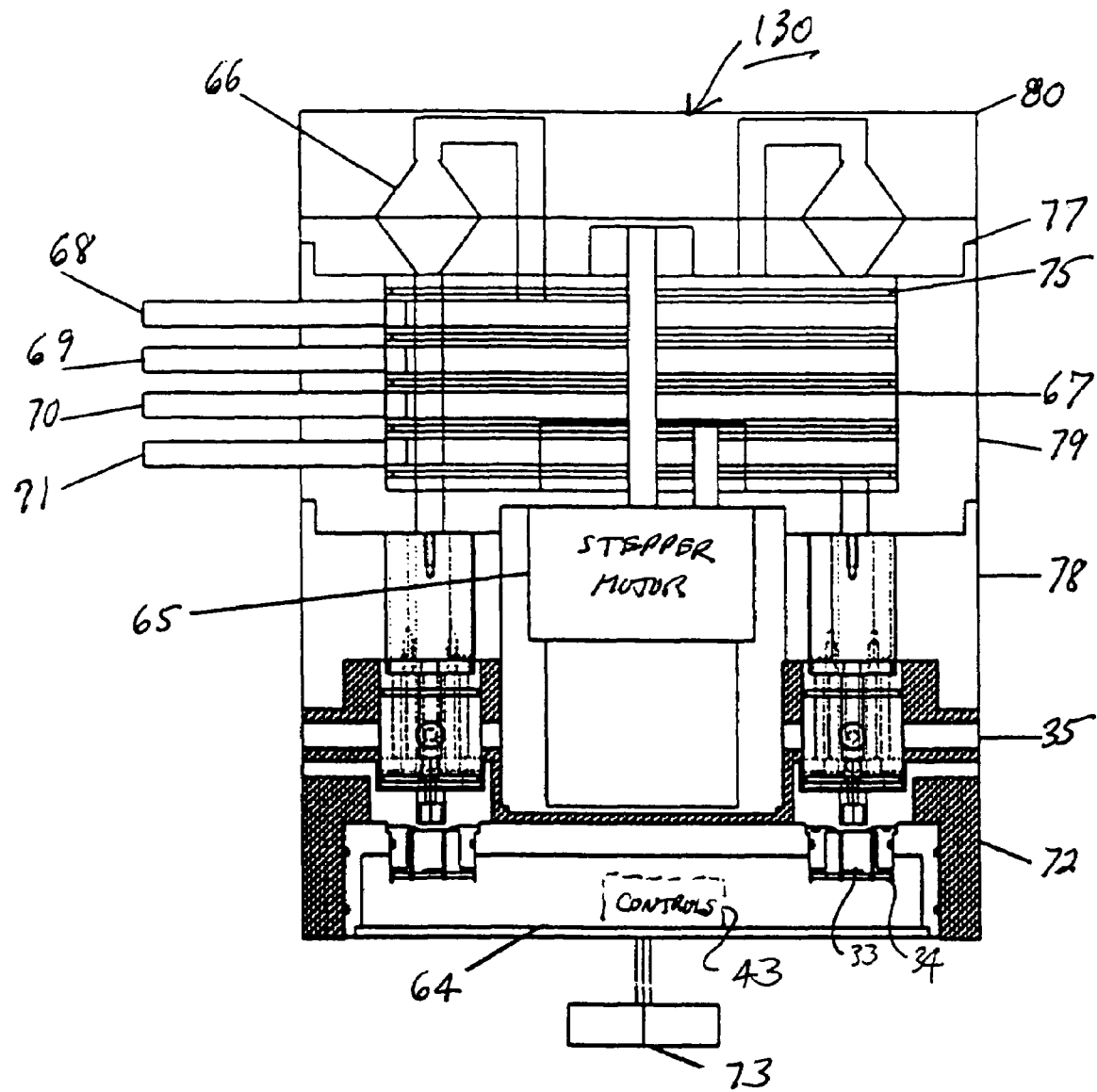

With reference now also to FIG. 5, the holder 34 with its respective crystal 33 is one of a plurality of, preferably eight, such crystals and these holders are mounted in a magazine 64. An external handle 73 is provided to enable the carousel to be both easily inserted into and removed from the support 72. The sample is directed to the respective crystal 33 by a rotating sampling valve 67.

The apparatus may be provided with a rotating sampling valve 67 to automatically switch the various sampling inlets 68, 69, 70, 71 to the corresponding sensor. The rotating sampling valve is controlled using a stepper motor 65 or other suitable electromechanical means. By rotating the valve, the sample inputs, which are illustrated at 68, 69, 70, 71, can be directed to any respective crystal 33 and a gravimetric filter 66. The top filter block 80 can be removed to facilitate filter changing.

Figure 6A:
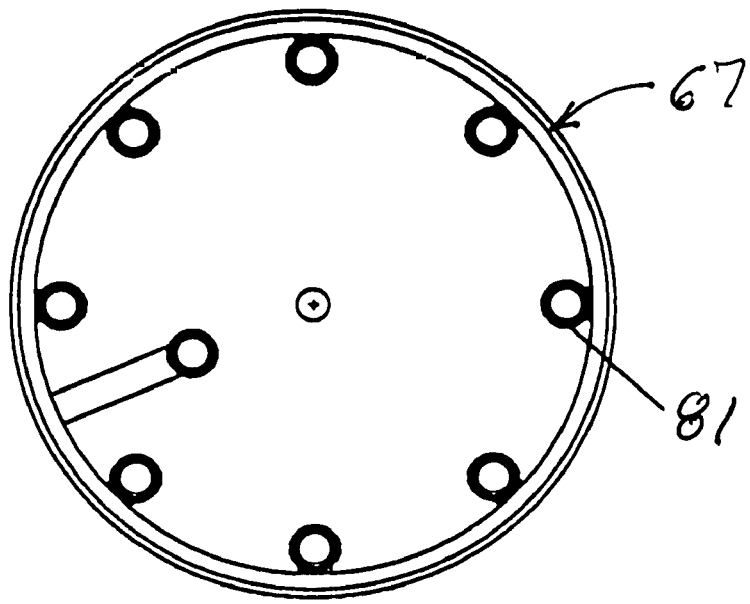
FIG. 6a is a top plan view of a rotating valve.
Figure 6B:
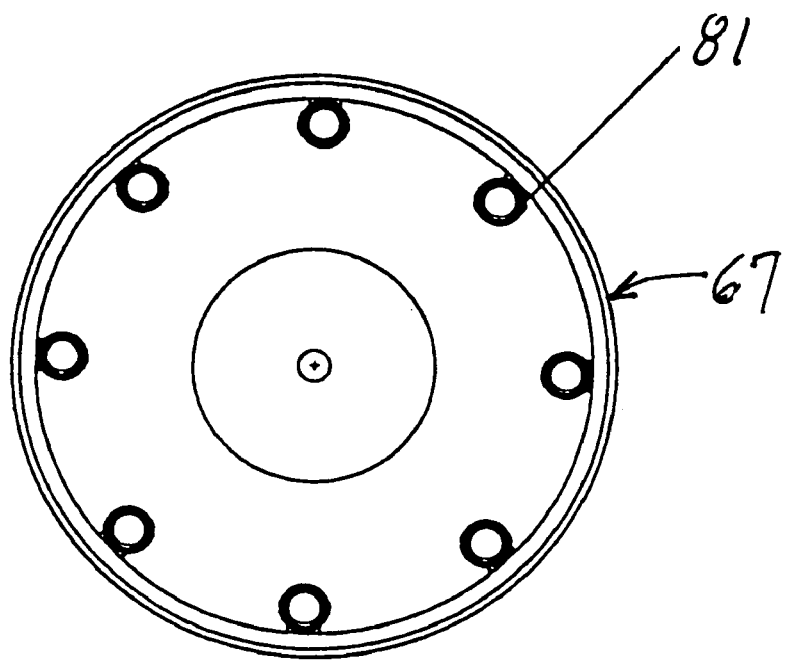

The valve rotating valve 67 is sealed to the bottom mounting block 78 and the top filter mounting block 77 using "o" rings 81 (FIG. 6). The valve rotating block 67 is also sealed to the valve outer block 79 by "o" rings 75.

With reference now also to FIG. 5, electronic controls 43 relating to the sensor 33 may be located within the carousel 64. The controls 64 include oscillator circuits 51 to drive and measure the crystal frequencies, heater controls 52 for the crystal temperatures, and sensors 53 for the measurement of corona current on the crystal exposed to the aerosol.

The apparatus is controlled through a main control 45.

Humidity compensation of the sampling sensor 33 can be achieved by simultaneously sampling a proportion of the filtered sample 74 to a second sensor 33.

Filter collection 66 can be made in parallel with the sensor 33 mass determination.

The control 45 may be programmed to automatically change the sampling crystal according to different parameters, for example:

1) when the crystal reaches its maximum mass loading,
2) after a specified time lapse,
3) after sampling in a particular location,
4) after sampling at particular inlet temperatures,
5) on manual (or other) external trigger.

The automatic changing of the crystal minimizes the limitations of the prior art apparatus associated with overloading the crystal, particle composition, and chemical properties of the particles.

Independent temperature control of the inlet 14 and the quartz crystal enables an assessment of the volatile/non-volatile components of the particles to be made. The control 45 also allows for the collection and storage temperatures of the crystals to be pre-programmed.

The multi-holder arrangement is not confined to a carousel and holders may be provided in a magazine in a linear array either side by side or in a stack.

The magazine, including the carousel, may be provided with an in-situ crystal cleaning system.

Changes and modifications in the specifically described embodiments can be carried out without departing from the principles of the invention which is intended to be limited only by the scope of the appended claims, as interpreted according to the principles of patent law including the doctrine of equivalents.

The invention claimed is:

1. Apparatus for the analysis of particles in an aerosol, comprising:
   at least one aerosol inlet and at least one electrostatic precipitator which directs an aerosol flow onto a mass sensor on which the particles are collected, the sensor being housed in a magazine including a plurality of other sensors each of which may be substituted for said sensor, and a control, said control selectively connecting one of said at least one aerosol inlet with one of said sensors.

2. Apparatus as claimed in claim 1 wherein each precipitator is mounted in an aperture in a support, and the magazine is movably mounted on the support so that sensors housed in the magazine may each be brought separately into alignment with the precipitator.

3. Apparatus as claimed in claim 2 wherein the magazine is in the form of a carousel and each sensor is aligned with a respective precipitator by indexing the carousel relative to the support.

4. Apparatus as claimed in claim 3 wherein the carousel, is rotatably mounted in a cylindrical recess in the support and is indexed by a motor operated by said control means.

5. Apparatus as claimed in claim 1 wherein the sensor is provided with a heater which is controllable to vary the temperature of the sensor which may be preset to any temperature as is desired.

6. Apparatus as claimed in claim 5 wherein sensor heater controls and mass monitoring controls are housed within the magazine.

7. Apparatus as claimed in claim 1 wherein said at least one precipitator has an inlet provided with a heater which is controllable to vary the inlet temperature.

8. Apparatus as claimed in claim 1 wherein the mass sensor is a piezoelectric quartz crystal.

9. Apparatus as claimed in claim 1 wherein said at least one sensor comprises at least two precipitators each being aligned with a respective sensor.

10. Apparatus as claimed in claim 9 wherein the respective inlets of said precipitators differ one from the other.

11. Apparatus as claimed in claim 10 wherein the inlets have different aerosol size classification properties.

12. Apparatus as claimed in claim 10 wherein one of said inlets is provided with a particle removal system.

13. Apparatus as claimed in claim 1 wherein said at least one aerosol inlet comprises a plurality of aerosol inlets.

14. Apparatus as claimed in claim 13 including a valve assembly, said valve assembly selectively connecting particular ones of said aerosol inlets with certain ones of the sensors.

15. Apparatus as claimed in claim 14 wherein said valve assembly comprises a rotary valve assembly.

16. Apparatus as claimed in claim 15 including an actuator for selectively rotating said rotary valve assembly.

17. A method of analyzing particle mass concentration of an aerosol which includes the use of apparatus as claimed in claim 1.

18. Apparatus for the analysis of particles in an aerosol and which comprises at least one electrostatic precipitator which directs an aerosol flow onto a mass sensor on which the particles are collected, the sensor being housed in a magazine including a plurality of other sensors each of which may be substituted for said sensor, and control means for automatically operating the magazine to effect a change of sensor.

* * * * *